United States Patent
Miyano et al.

(10) Patent No.: US 6,355,671 B1
(45) Date of Patent: Mar. 12, 2002

(54) SULFONATED DERIVATIVES OF CYCLIC PHENOL SULFIDES, PROCESS FOR THE PREPARATION THEREOF, SEPARATING AND RECOVERING AGENTS CONTAINING CYCLIC PHENOL SULFIDES, METHODS FOR SEPARATION AND RECOVERY THEREWITH, AND DRUG COMPOSITIONS CONTAINING THE SULFIDES

(75) Inventors: Sotaro Miyano; Nobuhiko Iki; Toyohisa Fujimoto, all of Miyagi; Fumio Hamada, Akita; Shingo Kato; Yoshiyuki Hiraishi, both of Tokyo; Hitoshi Kumagai, Saitama; Mitsuharu Hasegawa, Saitama; Setsuko Miyanari, Saitama; Yoshihiro Sugawa, Saitama; Masahiro Ishizuka, Saitama, all of (JP)

(73) Assignees: Cosmo Research Institute; Cosmo Oil Co., Ltd., both of Tokyo (JP)

(*) Notice: Subject to any disclaimer, the term of this patent is extended or adjusted under 35 U.S.C. 154(b) by 0 days.

(21) Appl. No.: 09/581,089

(22) PCT Filed: Dec. 8, 1998

(86) PCT No.: PCT/JP98/05549
§ 371 Date: Jun. 9, 2000
§ 102(e) Date: Jun. 9, 2000

(87) PCT Pub. No.: WO99/29683
PCT Pub. Date: Jun. 17, 1999

(30) Foreign Application Priority Data

Dec. 9, 1997 (JP) .............................. 9-354073
Feb. 26, 1998 (JP) ........................... 10-060346
Jun. 15, 1998 (JP) ........................... 10-181385
Jul. 15, 1998 (JP) ........................... 10-214756

(51) Int. Cl.⁷ ..................... A61K 31/38; C07D 339/00
(52) U.S. Cl. ........................ 514/430; 514/431; 549/1; 549/11
(58) Field of Search ............... 549/1, 11; 514/430, 514/431

(56) References Cited

U.S. PATENT DOCUMENTS 5,489,612 A * 2/1996 Atwood et al. .............. 514/569
5,824,808 A * 10/1998 Hori et al. ...................... 549/1

FOREIGN PATENT DOCUMENTS

EP 0 731 102 A1 9/1996
EP 0 851 935 A1 1/1998
WO WO 95/19974 7/1995
WO 98/09959 3/1998

OTHER PUBLICATIONS

T. Sone, et al., "Synthesis and Properties of Sulfur–Bridged Analogs of p–tert–Butylcalix[4]arene" Tetrahedron, vol. 53, No. 31, pp. 10689–10698, 1997.
Kumagai H., et al., "Facile Synthesis of p–tert–Butylthiacalix[4]arene by the Reaction of p–tert–Butylphenol with Elemental Sulfur in the Presence of a Base", Tetrahedron Lett., 38(22), 1997, pp. 3971–3972.
Zimmermann, H., et al., "Synthesis and dynamic NMR of hexathiadodecamethoxymetacyclophane", Tetrahedron, 44(1), 1988, pp. 277–279.
Bottino, F., et al., "Syntheses and properties of some polysulfur bridged metacyclophanes", Tetrahedron, 36(20–21), 1980, pp. 3095–3100.

* cited by examiner

Primary Examiner—Deborah C. Lambkin
(74) Attorney, Agent, or Firm—Sughrue Mion, PLLC

(57) ABSTRACT

A sulfonic acid compound of a cyclic phenol sulfide represented by formula (1):

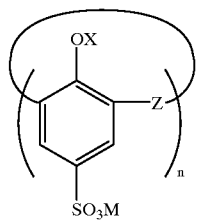

(1)

(wherein X represents a hydrogen atom, a hydrocarbon group, or an acyl group; M represents a hydrogen atom, an alkyl group, a metal, ammonium, (lower-alkyl)ammonium, (lower-alkanol)ammonium, a nitrogen-containing heterocyclic group, or an amino acid residue; Z represents Sm, SO, or $SO_2$; m is an integer of from 1 to 7; and n is an integer of from 4 to 12, with the proviso that the plural X's, M's and Z's are each the same or different, and at least one of the plural M's is neither a hydrogen atom nor an alkyl group), or a salt thereof; a composition for separating and recovering an organic halogen compound or a monocyclic aromatic compound, comprising a cyclic phenol sulfide or a salt thereof, and a carrier; and a pharmaceutical composition a cyclic phenol sulfide or a pharmaceutically acceptable salt, and a carrier.

12 Claims, 2 Drawing Sheets

CHLOROFORM

METHYLENE CHLORIDE

DICHLOROETHANE

TETRACHLOROETHANE

ABSCISSA IN FIG. 1a TO FIG. 1d : CONCENTRATION OF CYCLIC PHENOL SULFIDE ( III )

ORDINATE IN FIG. 1a TO FIG. 1d : CONCENTRATION OF ORGANIC HALOGEN COMPOUND IN HEAVY WATER AFTER STIRRING

US 6,355,671 B1

SULFONATED DERIVATIVES OF CYCLIC PHENOL SULFIDES, PROCESS FOR THE PREPARATION THEREOF, SEPARATING AND RECOVERING AGENTS CONTAINING CYCLIC PHENOL SULFIDES, METHODS FOR SEPARATION AND RECOVERY THEREWITH, AND DRUG COMPOSITIONS CONTAINING THE SULFIDES

This appln is a 371 of PCT/JP98/05549 Dec. 8, 1998.

TECHNICAL FIELD

The present invention relates to a novel cyclic phenol sulfide sulfonic acid compound, which can be used as a metal scavenger, an ion sensor, a separation membrane material, a substrate-specific sensor, a phase-transfer catalyst, an artificial enzyme, a light energy conversion material or an intermediate of a functional molecule capable of recognizing an ion or a molecule.

Furthermore, the present invention relates to a process for producing sulfonic acid of a cyclic phenol sulfide and a salt thereof, in which an alkyl group is directly replaced with a sulfonic group by reacting a cyclic alkylphenol sulfide with sulfuric acid.

Moreover, the present invention relates to a recovery agent and a recovery process of an organic halogen compound or a monocyclic aromatic compound which is deleterious in the living environment and the like, and relates to a novel agent for recovering an organic halogen compound or a monocyclic aromatic compound, which comprises a cyclic phenol sulfide, and a process for recovering an organic halogen compound or a monocyclic aromatic compounds by bringing the organic halogen compound or the monocyclic aromatic compound into contact with the cyclic phenol sulfide.

Also, the present invention relates to a medicament which uses a cyclic phenol sulfide as an active ingredient and to a composition comprising the same. More particularly, it relates to an antiviral agent, especially an anti-HIV agent having activity for retrovirus, such as HIV (human immunodeficiency virus) and the like.

BACKGROUND ART

Novel cyclic phenol sulfides completely different from the conventionally known non-cyclic phenol sulfide have been found, and a process for producing such cyclic phenol sulfides has also been found (JP-A-9-227553).

These cyclic phenol sulfides include a compound having a sulfonic group at the p-position on the benzene ring based on the hydroxyl group. However, in order to produce cyclic phenol sulfide sulfonic acid to which a sulfonic group is introduced at the p-position of the benzene ring based on the hydroxyl group, it is necessary to employ two step reactions for once carrying out dealkylation of a cyclic alkylphenol sulfide by replacing the alkyl group with a hydrogen atom and then sulfonating it using fuming sulfuric acid or the like, so that a high production yield cannot be expected and its production sometimes requires a prolonged period of time.

Also, environmental pollution by organic halogen compounds including trihalomethanes and the like whose carcinogenicity has been pointed out and monocyclic aromatic compounds, such as phenol and the like, becomes a problem in recent years, so that their effective elimination processes have been expected.

For example, organic halogen compounds, such as 1,1,1-trichloroethane and the like, are broadly used mainly as detergents in industries, such as automobile, electronic, electric, precision instrument, and the like, but cause serious problems regarding environmental pollution due to that they flow into rivers through contaminated waste water from factories or the compound once evaporated into the air is mixed with rain water and contaminate underground water and soil. Additionally, so-called trihalomethanes, such as chloroform, dibromochloroethane and the like, are contained in tap water as disinfection by-products of tap water and well known as carcinogenic substances as described above. Carcinogenicity of benzene regarded as one of air pollutants has also been pointed out.

With regard to these organic halogen compounds and monocyclic aromatic compounds, such as benzene and the like, their respective regulated values are specified by the water environment standard, as well as the water pollution control law and effluent standard, water supply law and water quality standard of tap water, sewage water law and sewage water effluent standard, and soil environment standard.

Additionally, among monocyclic aromatic compounds, for example, phenol can be regarded as a cause of water pollution due to that there is a possibility that a small amount of underground water and the like is contaminated in industrial waste water and soil.

A process for recovering contaminants can be exemplified as an important process for solving such environmental pollution. Accordingly, research and development have been attempted on various separation recovery techniques, such as membrane separation techniques, extraction techniques, and the like, but concern has been directed toward a pollutant recovering process which is more efficient, an energy-saving type, inexpensive, and easy to handle.

AIDS (acquired immunodeficiency syndrome) is now world-widely considered to be one of the greatest threats which spoil human life and health. The number of AIDS patients reported to WHO (the World Health Organization) until the end of December, 1994 is 1,020,000, but it is said that its actual number is assumed to be approximately 4,500,000, and it is said also that the number of infected people reaches 4 to 5 times of the actual patients.

Accordingly, studies on the AIDS virus, namely HIV, are actively carried out with various objects, such as elucidation of the origin of HIV and its structure including gene structure of the virus, elucidation of the infection route, protection of infection, diagnosis, treatment, prevention of infection, and the like.

HIV contains RNA as the gene, and belongs to retrovirus which breaks into a host and transcripts its genetic information from RNA to DNA by a reverse transcriptase to the opposite direction of ordinary transcription. The HIV-concerning infection cycle has been fairly elucidated.

Consequently, studies have been carried out actively on the development of anti-AIDS agents considered to have effects on respective steps of the infection cycle. That is, the anti-HIV agents include an adsorption inhibitor, an uncoating inhibitor, a reverse transcription inhibitor, an integration inhibitor, a transcription translation inhibitor, an HIV protease inhibitor and the like. Peptide polymer substances considered to have a neutralization activity and sulfated polysaccharides considered to have an activity to coat virus particles physically have been developed as the adsorption inhibitor; cyclic polyamine compounds as the uncoating inhibitor; and nucleoside compounds, such as AZT and the like, and non-nucleoside compounds, such as TIBO compound and the like, as the reverse transcription inhibitor.

However, the anti-HIV agents have serious problems still unsolved, namely strong side effects, such as neurological disorder, organ function disorder, and the like, and their high expression frequency and generation of respective resistant strains after prolonged period of administration.

Recently, development of protease inhibitors has been carried out actively. While the reverse transcription inhibitor inhibits HIV-DNA formation, the protease inhibitor inhibits processing of HIV constitutive protein. Accordingly, use of both inhibitors in combination can inhibit the copying of virus by the protease inhibitor which have not been inhibited by the reverse transcription inhibitor, so that their high combined effect is expected.

However, even in the case of the protease inhibitor, side effects, such as lipemia and the like, have been pointed out so that it is not free from the problem of side effects, and it also has a problem of being considerably expensive as a drug.

That is, a substantially inexpensive drug which is superior in anti-HIV activity and the like, causes less side effects and can be produced by a simple and easy production process is desired.

DISCLOSURE OF THE INVENTION

An object of the present invention is to provide a cyclic phenol sulfide sulfonic acid compound represented by formula (1).

Also, an object of the present invention is to provide a process for producing sulfonic acid of a cyclic phenol sulfide, and a salt thereof, in which the alkyl group of a cyclic alkylphenol is directly replaced with a sulfonic group using sulfuric acid as a sulfonation agent at a high yield, efficiently and easily.

Furthermore, an object of the present invention is to provide, in a technique for recovering organic halogen compounds or monocyclic aromatic compounds which are typical environmental pollution substances, a separation recovery agent which has a conventionally unknown and completely new structure and has excellent recovery capacity of an organic halogen compound or a monocyclic aromatic compounds, and a separation recovery process.

Moreover, an object of the present invention is to provide a medicament, particularly an antiviral agent, which has an antiviral activity, is low in cytotoxicity, can be produced by an easy and simple process, and is inexpensive.

That is, the present invention relates to a sulfonic acid compound of a cyclic phenol sulfide represented by formula (1):

(1)

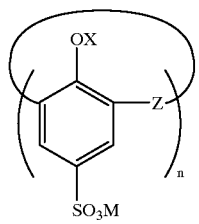

(wherein X represents a hydrogen atom, a hydrocarbon group, or an acyl group;

M represents a hydrogen atom, an alkyl group, a metal, an ammonium, a (lower-alkyl)ammonium, a (lower-alkanol)ammonium, a nitrogen-containing heterocyclic group, or an amino acid residue;

Z represents Sm, SO, or SO$_2$;

m is an integer of from 1 to 7; and n is an integer of from 4 to 12, with the proviso that the plural X's, M's and Z's are each the same or different, and at least one of the plural M's is neither a hydrogen atom nor an alkyl group).

Furthermore, the present invention relates to a process for producing sulfonic acid of a cyclic phenol sulfide or a salt thereof, comprising reacting a cyclic alkylphenol sulfide represented by formula (2):

(2)

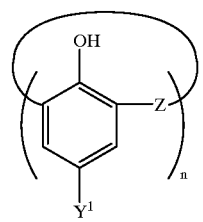

(wherein Y$^1$ represents an alkyl group, and Z and n have the same meanings as defined above) with sulfuric acid to produce sulfonic acid of a cyclic phenol sulfide represented by formula (3):

(3)

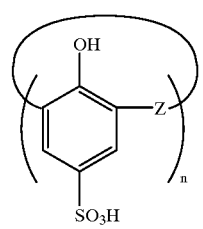

(wherein Z and n have the same meanings as defined above), or a salt thereof.

Moreover, the present invention relates to a composition for separating and recovering an organic halogen compound or a monocyclic aromatic compound, which comprises a compound represented by formula (4):

(4)

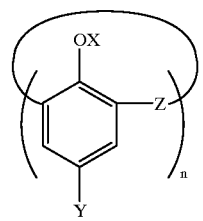

(wherein X, Z and n have the same meanings as defined in formula (1);

Y represents a hydrogen atom, a hydrocarbon group, a halogenated hydrocarbon group, —COR$^1$, —OR$^2$, —COOR$^3$, —CN, —CONH$_2$, —NO$_2$, —NR$^4$R$^5$, a halogen atom, —SO$_4$R$^6$, —SO$_3$R$^7$, or —SO$_3$M;

R$^1$ to R$^7$ are a hydrogen atom or a hydrocarbon group; and

M has the same meaning as defined in formula (1), with the proviso that the plural X's, Y's and Z's are each the same or different), or a salt thereof, and a carrier.

Also, the present invention relates to a process for separating and recovering an organic halogen compound or a monocyclic aromatic compound, comprising bringing a compound represented by formula (4) or a salt thereof into contact with an organic halogen compound or a monocyclic aromatic compound to separate and recover the organic halogen compounds or the monocyclic aromatic compound.

Still furthermore, the present invention relates to a composition which comprises a compound represented by formula (4) or a pharmaceutically acceptable salt thereof, and a pharmaceutically acceptable carrier or diluent.

Still moreover, the present invention relates to use of a compound represented by formula (4) or a pharmaceutically acceptable salt thereof for prevention or treatment of a disease caused by a virus production.

Additionally, the present invention relates to a process for preventing or treating a disease caused by a virus production, comprising administering an effective amount of a compound represented by formula (4) or a pharmaceutically acceptable salt thereof to a human or an animal (e.g., mammals).

Still additionally, the present invention relates to a process for selectively inhibiting a virus production, comprising administering an effective amount of a compound represented by formula (4) or a pharmaceutically acceptable salt thereof to cells.

BEST MODE FOR CARRYING OUT THE INVENTION

Figure 1A:
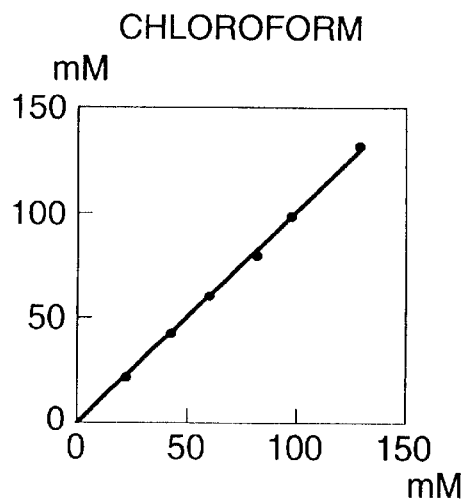
FIG. 1 is a graph showing changes in the concentration of organic halogen compounds contained in heavy water, measured by changing a concentration of a cyclic phenol sulfide (III) in its heavy water solution and saturating each of the heavy water solutions with each of the organic halogen compound.
Figure 1B:
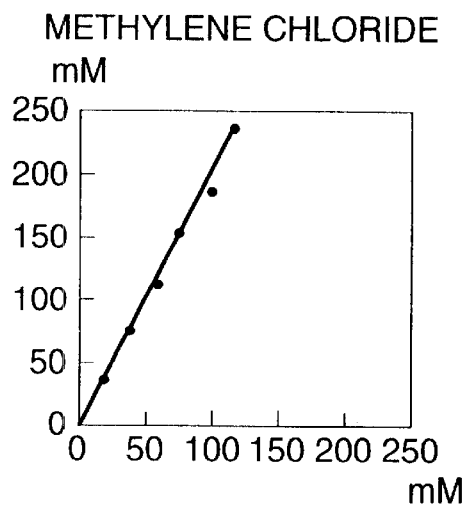
Figure 1C:
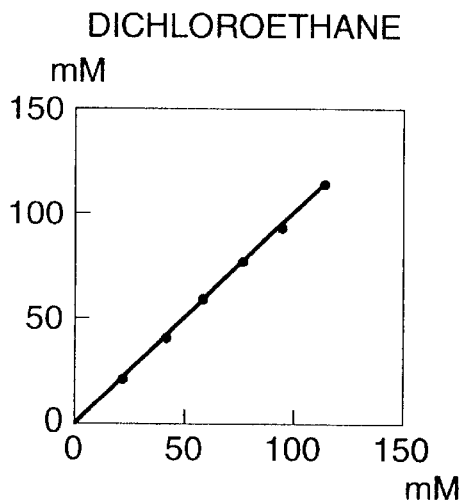
Figure 1D:
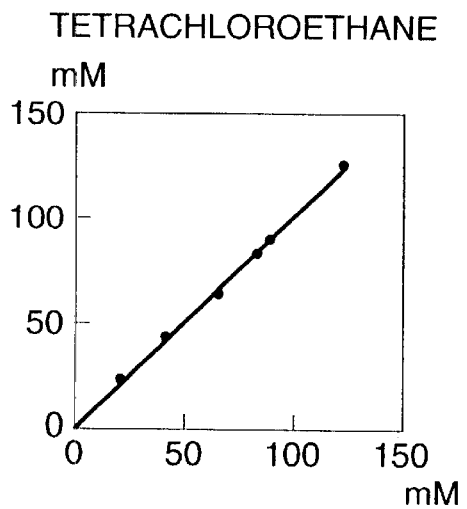

In order to achieve the above-described objects, the inventors of the present invention have conducted intensive studies and found a process for efficiently producing a cyclic phenol sulfide to which a sulfonic acid or a sulfonic acid salt is incorporated, comprising reacting a cyclic phenol sulfide having an alkyl group-containing phenol as its constituting unit with sulfuric acid and then salting out the reaction product, sulfonic acid of the cyclic phenol sulfide. Thus, the present invention has been accomplished.

Furthermore, in order to establish the above-described efficient process for separating and recovering an organic halogen compound or a monocyclic aromatic compound, they have conducted intensive studies and found that a compound represented by formula (4) can form an inclusion compound with an organic halogen compounds or a monocyclic aromatic compound. Thus, the present invention has been accomplished.

Also, taking note of the fact that the cyclic phenol sulfide has a sulfide bond and is capable of incorporating an organic compound to its cyclic structure, they have conducted intensive studies and found that a compound represented by formula (4) has antiviral activities, particularly against retrovirus, such as HIV or the like. Thus, the present invention has been accomplished.

The present invention will be explained below in detail.

In formula (1) or (4), X represents a hydrogen atom, a hydrocarbon group, or an acyl group.

The carbon atom number of the hydrocarbon group is not particularly limited so long as the number is 1 or more. It is preferably from 1 to 30, more preferably from 1 to 18, still more preferably from 1 to 8, and most preferably from 1 to 6. Examples of the hydrocarbon group include a saturated aliphatic hydrocarbon group, an unsaturated aliphatic hydrocarbon group, an alicyclic hydrocarbon group, an alicyclic-aliphatic hydrocarbon group, an aromatic hydrocarbon group, an aromatic-aliphatic hydrocarbon group, and the like.

Preferred examples of the saturated aliphatic hydrocarbon group include an alkyl group, such as methyl, ethyl, n-propyl, isopropyl, n-butyl, isobutyl, tert-butyl, n-pentyl, neopentyl, n-hexyl, n-octyl, tert-octyl, n-nonyl, isononyl, n-dodecyl, and the like; a hydrocarbon group derived from a polymer or copolymer of ethylene, propylene, or butylene; and the like. The alkyl group include straight, branched and cyclic alkyl groups.

Preferred examples of the unsaturated aliphatic hydrocarbon group include alkenyl and alkynyl groups, such as vinyl, allyl, isopropenyl, 2-butenyl, and the like; a hydrocarbon group derived from a polymer or copolymer of acetylene, butadiene, or isoprene; and the like.

Preferred examples of the alicyclic hydrocarbon group include cycloalkyl, cycloalkenyl, cycloalkynyl groups, and the like, such as cyclohexyl, methylcyclohexyl, ethylcyclohexyl, and the like.

Preferred examples of the alicyclic-aliphatic hydrocarbon group include cycloalkyl-, cycloalkenyl-, or cycloalkynyl-substituted alkyl, alkenyl, and alkynyl groups, and the like, such as cyclohexylmethyl, cyclohexylethyl, and the like.

Preferred examples of the aromatic hydrocarbon group include an aryl group, such as phenyl, naphthyl, and the like; an alkylaryl group, such as methylphenyl, dimethylphenyl, trimethylphenyl, ethylphenyl, butylphenyl, and the like; and the like.

Preferred examples of the aromatic-aliphatic hydrocarbon group include an aralkyl group and the like, such as benzyl, phenylethyl, phenylpropyl, phenylbutyl, methylphenylethyl, and the like.

Also, the above-described hydrocarbon group may be substituted with a substituent, such as $-COR^{11}$, $-OR^{12}$, $-COOR^{13}$, $-CN$, $-CONH_2$, $-NO_2$, $-NR^{14}R^{15}$, a halogen atom, $-SO_4R^{16}$, $-SO_3R^{17}$, or the like. In this connection, $R^{11}$ to $R^{17}$ represent a hydrogen atom or a group similar to the above-described hydrocarbon group.

The carbon atom number of the acyl group is not particularly limited so long as the number is 1 or more. Preferably, the carbon atom number of the acyl group is preferably from 1 to 9, more preferably from 1 to 7. Preferred examples of the acyl group include formyl, acetyl, propionyl, butyryl, valeryl, oxalyl, malonyl, succinyl, benzoyl, acryloyl, methacryloyl, crotonyl, and the like.

Furthermore, the acyl group may be substituted with the substituent exemplified in the above-described hydrocarbon group.

In formula (1) or (4), the number of X's present is from 4 to 12 per molecule. The plural X's are the same or different.

In formula (1) or (4), M represents a hydrogen atom, an alkyl group, a metal, an ammonium, a (lower-alkyl)ammonium, a (lower-alkanol)ammonium, a nitrogen-containing heterocyclic group, an amino acid residue, or the like. They may be substituted with the substituent exemplified in the above-described hydrocarbon group.

Examples of the alkyl group include groups similar to the alkyl groups exemplified in the above-described X.

Examples of the metal include an alkali metal, such as sodium, potassium, and the like; an alkaline earth metal salt, such as calcium, magnesium, and the like; and the like.

Preferably, the (lower-alkyl)ammonium of M has an alkyl moiety of a carbon number of from 1 to 12, and examples thereof include methylammonium, ethylammonium, n-propylammonium, isopropylammonium, n-butylammonium, isobutylammonium, sec-butylammonium, tert-butylammonium, dimethylammonium, diethylammonium, di-n-propylammonium, diisopropylammonium, di-n-butylammonium, diisobutylammonium, di-sec-butylammonium, di-tert-butylammonium, trimethylammonium, triethylammonium, tetramethylammonium, tetraethylammonium, tetraethylammonium, cyclopropylammonium, cyclopentylammonium, cyclohexylammonium, phenylmethylammonium, phenylethylammonium, phenylpropylammonium, benzyltrimethylammonium, phenyltriethylammonium, and the like.

Preferably, the (lower-alkanol)ammonium of M has an alkyl moiety of from 1 to 10, and examples thereof include ethanolammonium, diethanolammonium, triethanolammonium, and the like.

Examples of the nitrogen-containing heterocyclic group of M include a pyridinium salt, such as pyridinium, N-methylpyridinium, and the like; piperidino, piperazino, 1-methylpirazino, 4-ethylmorpholino, and the like.

The amino acid residue of M means a monovalent substituent derived from an amino acid, and examples thereof include a substituent and the like in which a hydrogen atom is added to an amino group of an amino acid, such as glycine, phenylalanine, glutamic acid, lysine, and the like.

In formula (1), the number of sulfonic acid salts present is from 4 to 12 per molecule. When the plural sulfonic acid salts are present in the molecule, the plural sulfonic acid salts are the same or different.

In formula (1) or (4), Z represents Sm, SO, or $SO_2$.

Furthermore, in formula (1) or (4), the number of Z's present is from 4 to 12 per molecule. The plural Z's are the same or different.

In formula (1) or (4), m is an integer of from 1 to 7, and preferably 1 or 2.

In formula (1) or (4), n is an integer of from 4 to 12, and preferably from 4 to 8.

In formula (4), Y represents a hydrogen atom, a hydrocarbon group, a halogenated hydrocarbon group, $—COR^1$, $—OR^2$, $—COOR^3$, —CN, $—CONH_2$, $—NO_2$, $—NR^4R^5$, a halogen atom, $—SO_4R^6$, $—SO_3R^7$, or $—SO_3M$. The plural Y's are the same or different.

In this connection, examples of the hydrocarbon group and $—COR^1$ of Y include those similar to the hydrocarbon group and acyl group explained in the above-described X, and preferred examples thereof are similar. Furthermore, examples of the halogenated hydrocarbon group include those similar to the hydrocarbon group explained in the above-described X with which a halogen atom is substituted, and preferred examples thereof are similar. Moreover, the above-described hydrocarbon group may be substituted with the substituent exemplified in the hydrocarbon group represented by the above-described X.

$R^1$ to $R^7$ are a hydrogen atom or a hydrocarbon group. The hydrocarbon group includes those similar to the hydrocarbon group explained in the above-described X, and preferred examples thereof are similar. Also, the above-described hydrocarbon group may be substituted with the substituent exemplified in the hydrocarbon group represented by the above-described X.

The compound represented by formula (4) may form a sulfonic acid salt similar to formula (1). Furthermore, the compound represented by formula (4) may form a salt other than a sulfonic acid salt, or a pharmaceutically acceptable salt. Examples of the salt and the pharmaceutically acceptable salt include a carboxylic acid salt. Examples of the carboxylic acid salt include a salt of carboxylic acid or alkylcarboxylic acid with the above-described M. The carbon number of the alkyl group of alkylcarboxylic acid salt is not particularly limited so long as it is 1 or more. Preferably, it is 10 or less.

When the compound represented by formula (1) or (4) contains an isomer, such as a positional isomer, a stereoisomer, an enantiomer, or a tautomer, the present invention includes possible isomers and mixtures thereof at any ratios.

Furthermore, the compound represented by formula (1) or (4) may be present as a hydrate or a solvate in the form of an adduct with water or various solvents.

In formula (2), $Y^1$ represents an alkyl group. The number of $Y^1$'s present is not particularly limited so long as it is 1 or more. It is preferably from 1 to 30, and more preferably from 1 to 12.

Furthermore, the alkyl group is preferably a tertiary hydrocarbon group, and more preferably a tert-butyl group.

A process for producing a cyclic phenol sulfide represented by formula (2) in which Z is Sm is described in JP-A-9-227553. An appropriate process is a process comprising first reacting a phenol compound represented by formula (5) in which a phenol having an alkyl group at the p-position of the benzene ring based on a hydroxyl group:

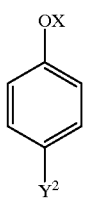

(5)

(wherein $Y^2$ represents an alkyl group) with an appropriate amount of elemental sulfur in the presence of an appropriate amount of at least one metallic reagent selected from an alkali metal reagent and an alkaline earth metal reagent.

The phenol compound and elemental sulfur used as starting materials are fed in such a proportion that the amount of the elemental sulfur is 0.1 gram equivalent or more, preferably 0.35 gram equivalents or more, per gram equivalent of the phenol compound. Although there is no particular upper limit on the proportion of the elemental sulfur fed as a starting material, the amount thereof is preferably 20 gram equivalents or less, particularly preferably 10 gram equivalents or less, per gram equivalent of the phenol compound.

Examples of the alkali metal reagent include an elemental alkali metal, an alkali metal hydride, an alkali metal hydroxide, an alkali metal carbonate, an alkali metal alkoxide, an alkali metal halide, and the like. Examples of the alkaline earth metal reagent include an elemental alkaline earth metal, an alkaline earth metal hydride, an alkaline earth metal hydroxide, an alkaline earth metal oxide, an alkaline earth metal carbonate, an alkaline earth metal alkoxide, an alkaline earth metal halide, and the like.

The alkali metal reagent or the alkaline earth metal reagent is used at an amount of 0.005 gram equivalents or more, preferably 0.01 gram equivalent or more, per gram equivalent of the phenol compound. Although there is no particular upper limit on the amount used of the alkali metal reagent or the alkaline earth metal reagent, the amount thereof is preferably 10 gram equivalents or less, and more preferably 5 gram equivalents or less.

A process for converting a compound disclosed in WO 98/09959 may be used as a process for converting a compound in which the cyclic phenol sulfide of formula (2) in which Z is S to a compound in which Z is SO or $SO_2$. That is, the compound is converted to a compound in which Z is SO or $SO_2$ using an appropriate oxidizing agent, such as hydrogen peroxide, an organic peroxide, peracid, a halogen oxide, oxygen, ozone, nitric acid, an inorganic oxide, and the like. Also, when Z is Sm (m is 2 or more), the conversion can be carried out in the same manner.

Sulfonic acid of a cyclic phenol sulfide can be synthesized by suspending the thus produced cyclic alkyl phenol sulfide represented by formula (2) in sulfuric acid, followed by heating under stirring.

The concentration of the sulfuric acid used may be 80% or more, and preferably 90% or more.

The amount used of the sulfuric acid is not particularly limited; however, it is generally from 5 to 200 ml per gram of the cyclic alkyl phenol sulfide.

The reaction temperature is preferably 70° C. or more, and more preferably 80° C. or more. The upper limit of the reaction temperature can be selected so long as the compound of formula (2) is not decomposed. Preferably, it is preferably 170° C. or less.

The reaction time is not particularly limited; however, it is generally from 2 to 30 hours. However, since the decomposition reaction of the starting material progresses along with the reaction, a reaction for too long time is not preferred.

In the present invention, the sulfonic acid of a cyclic phenol sulfide obtained in the above reaction may be collected as a final product, and alternatively, the sulfonic acid salt of a cyclic phenol sulfide may be collected as a final product.

Also, as a production process of a compound of formula (1) in which Z is SO or $SO_2$, Z in a compound of formula (2) in which Z is Sm can be converted to SO or $SO_2$ using an appropriate oxidant after replacement of an alkyl group to a sulfone group.

Examples of the sulfonic acid salt of a cyclic phenol sulfide according to the present invention include an inorganic salt of sulfonic acid of a cyclic phenol sulfide and an organic salt of sulfonic acid of a cyclic phenol sulfide. Examples of the inorganic salt of sulfonic acid of a cyclic phenol sulfide include a metal salt of sulfonic acid of a cyclic phenol sulfide, an ammonium salt of sulfonic acid of a cyclic phenol sulfide, and the like. Examples of the metal salt of sulfonic acid of a cyclic phenol sulfide include an alkali metal salt, such as a sodium salt, a potassium salt, and the like, of a cyclic phenol sulfide; an alkaline earth metal salt, such as a calcium salt, a magnesium salt, and the like, of a cyclic phenol sulfide; and the like. Examples of the inorganic salt of sulfonic acid of a cyclic phenol sulfide include a (lower-alkyl)ammonium salt, a (lower-alkanol)ammonium salt, a pyridinium salt, an amino acid salt of sulfonic acid of a cyclic phenol sulfide, and the like.

In formula (3), the number of sulfonic acid groups present is from 4 to 12 per molecule. In the a sulfonic acid salt of a cyclic phenol sulfide, at least one sulfonic acid group in the sulfonic acid groups in formula (3) may form a sulfonic acid salt, and all sulfonic acid groups may form sulfonic acid salts. If the plural sulfonic acid salts are present per molecule, they are the same or different.

Preferred examples of a production process of a sulfonic acid salt of a cyclic phenol sulfide include a process comprising diluting, with water, sulfonic acid of a cyclic phenol sulfide which is a reaction product after termination of the above reaction, subjecting the diluted sulfonic acid to salting out using a metal salt, such as an alkali metal, an alkaline earth metal, and the like, an ammonium salt, a (lower-alkyl)ammonium salt, a (lower-alkanol)ammonium salt, or a pyridinium salt according to the ordinary process to obtain crystals of the metal salt, the (lower-alkyl)ammonium salt, the (lower-alkanol)ammonium salt or the pyridinium salt of sulfonic acid of a cyclic phenol sulfide represented by formula (3). Examples of the alkali metal salt include a halogenated alkali metal salt, such as an alkali metal carbonic acid salt, an alkali metal chloride, and the like. Examples of the alkaline earth metal salt include a halogenated alkaline earth metal salt, such as an alkali metal carbonic acid salt, an alkaline earth metal salt, and the like. Examples of the (lower-alkyl) ammonium salt include a methylamine hydrochloric acid salt, an ethylamine-hydrochloric acid salt, an n-butylamine hydrochloric acid salt, an n-propylamine hydrochloric acid salt, an isopropylamine hydrochloric acid salt, a dimethylamine hydrochloric acid salt, a diethylamine hydrochloric acid salt, a di-n-butylamine hydrochloric acid salt, a diisobutylamine hydrochloric acid salt, a di-sec-butylamine hydrochloric acid salt, di-tert-butylamine hydrochloric acid salt, a di-n-propylamine hydrochloric acid salt, a diisopropylamine hydrochloric acid salt, a trimethylamine hydrochloric acid salt, a triethylamine hydrochloric acid salt, a tri-n-butylamine hydrochloric acid salt, a triisobutylamine hydrochloric acid salt, a tri-n-propylamine hydrochloric acid salt, and the like. Examples of the (lower-alkanol)ammonium salt include an ethanolamine hydrochloric acid salt, a diethanolamine hydrochloric acid salt, a triethanolamine hydrochloric acid salt, and the like. Examples of the pyridinium salt include a pyridine hydrochloric acid salt, an N-methylpyridinium halogenide, and the like.

The hydrogen atom of a hydroxyl group in the sulfonic acid compound of a cyclic phenol sulfide can be optionally converted to a hydrocarbon group or an acyl group by etherification or acylation. Such a conversion process is disclosed in JP-A-9-227553, and includes a process comprising substituting a hydrogen atom of a hydroxyl group in a cyclic phenol sulfide with an alkali metal, and reacting the alkali metal with a hydrocarbon to substitute it with a hydrocarbon according to the Williams reaction, and a process comprising converting it to an acyl group with an acylating agent, such as acetyl chloride, acetic anhydride, and the like.

If the reaction product is a mixture, the mixture can be separated by, for example, recrystallization or use of the difference of solubility, according to the ordinary process.

The cyclic phenol sulfide of formula (4) can be produced, for example, according to a process disclosed in JP-A-9-227553 or the above-described process.

The agent of the present invention for separating and recovering an organic halogen compound or a monocyclic aromatic compound comprises a compound of the above-described formula (4).

The agent of the present invention for separating and recovering an organic halogen compound or a monocyclic aromatic compound may comprise a compound of the above-described formula (4) alone or together with other component. Also, its form may be any form, such as solid, liquid, solution, or the like.

When the agent of the present invention for separating and recovering an organic halogen compound or a monocyclic aromatic compound is brought into contact with an organic halogen compound or a monocyclic aromatic compound, an inclusion compound of a cyclic phenol sulfide contained in the separation recovery agent with the organic halogen compound or the monocyclic aromatic compounds is formed, so that the organic halogen compound or the monocyclic aromatic compound can be recovered.

In this connection, according to the present invention, both of the organic halogen compound and the monocyclic aromatic compound can be simultaneously separated and recovered by bringing the agent for separating and recovering an organic halogen compound or a monocyclic aromatic compound into contact with both of the organic halogen compound and the monocyclic aromatic compound simultaneously.

The form of the organic halogen compound or the monocyclic aromatic compound brought into contact with the agent of the present invention for separating and recovering an organic halogen compound or a monocyclic aromatic compound may be any form, such as a solid, a liquid, a solution, and the like.

Examples of the organic halogen compound which can be recovered according to the present invention include methylene chloride, dichloromethane, chloroform, dibromochloromethane, bromodichoromethane, bromoform, carbon tetrachloride, vinyl chloride, 1,1-dichloroethylene, cis-1,2-dichloroethylene, trans-1,2-dichloroethylene, trichloroethylene, tetrachloroethylene, 1,1-dichloroethane, 1,2-dichloroethane, 1,1,1-trichloroethane, 1,1,2-trichloroethane, dibromochloroethane, chlorobenzene, PCB, 1,3-dichloropropene, and the like.

Examples of the monocyclic aromatic compound which can be recovered according to the present invention include benzene, toluene, xylene, phenol, and the like.

The organic halogen compound or the monocyclic aromatic compound may be alone or a mixture of two or more.

When the organic halogen compound or the monocyclic aromatic compound brought into contact with the agent of the present invention for separating and recovering an organic halogen compound or a monocyclic aromatic compound is in the form of a solution, the concentration of the organic halogen compound or the monocyclic aromatic compound is not particularly limited.

Examples of a preferred process for bringing the agent of the present invention for separating and recovering of an organic halogen compound or a monocyclic aromatic compound into contact with an organic halogen compound or a monocyclic aromatic compound is a process in which an organic halogen compound, a monocyclic aromatic compound or a solution comprising the same is mixed with a compound represented by formula (4) or a solution in which the compound is dissolved.

In this case, preferably, X of formula (4) is hydrogen and Y is —$SO_3M$, and water is preferred as the solvent.

When the organic halogen compound or the monocyclic aromatic compound is alone, it may be mixed directly with a cyclic phenol sulfide solution, and when the organic halogen compound or the monocyclic aromatic compound is contained in a solution, the solution may be mixed with a cyclic phenol sulfide alone or with a cyclic phenol sulfide sulfonic acid compound solution.

The concentration of the compound represented by formula (4) in its solution is not particularly limited, except that the upper limit is restricted by the solubility of the compound.

The operation for mixing the agent of the present invention for separating and recovering an organic halogen compound or a monocyclic aromatic compound with an organic halogen compound or a monocyclic aromatic compound can be carried out, for example, by subjecting a cyclic phenol sulfide or its solution and an organic halogen compound, a monocyclic aromatic compound or a solution comprising the same to various agitation operations, such as shaking, stirring, and the like. The shaking and stirring conditions are not particularly limited, and the compounds after mixing may be allowed to stand.

Various processes can be employed as the process for recovering an organic halogen compound or a monocyclic aromatic compounds from the mixture; for example, precipitation separation of the inclusion compound of the cyclic phenol sulfide and the organic halogen compound or the monocyclic aromatic compound by salting out or the like can be exemplified as a process when the solvent is water. When the solvent is not water, the inclusion compound of the cyclic phenol sulfide and the organic halogen compound or the monocyclic aromatic compound can be recovered by evaporating the solvent.

Another example of the preferred process of the present invention for separating and recovering an organic halogen compound or a monocyclic aromatic compound is a process in which a separation recovering agent containing a compound represented by formula (4) is mixed with or supported on a carrier, and an organic halogen compound or a monocyclic aromatic compound is separated and recovered by bringing the organic halogen compound or the monocyclic aromatic compound into contact therewith. An example of this process includes a process in which an organic halogen compound or a monocyclic aromatic compound is separated and recovered using separation means, such as a separation membrane, column chromatography, or the like, and the separation recovering agent of the present invention is mixed with or supported on a carrier.

Still another example of the preferred process of the present invention for separating and recovering an organic halogen compound or a monocyclic aromatic compound is a process in which a separation recovering agent comprising the cyclic phenol sulfide is dissolved in a solution comprising an organic halogen compound or a monocyclic aromatic compound in advance, and the organic halogen compound or the monocyclic aromatic compound is separated and recovered by bringing the resulting solution into contact with a carrier to adsorb the inclusion compound.

Examples of the carrier include a solid carrier and the like, such as silica gel, an ion exchange resin, glass, carbon, diatomaceous earth, cellulose, and the like. Although not particularly limited, silica gel and a basic anion exchange resin are preferred. As the process in which a separation recovering agent comprising a cyclic phenol sulfide is mixed with or supported on a carrier, any known process can be used, such as a process in which the agent is supported on silica gel or an ion exchange resin by chemical adsorption.

The temperature for bringing a cyclic phenol sulfide or its solution into contact with an organic halogen compound or a monocyclic aromatic compound or a solution comprising the same is not particularly limited, so long as it is a boiling point or less of the solvent, and in the case of water, for example, the reaction may be generally carried out approximately at from room temperature to 60° C.

In this connection, the carrier which adsorbed the inclusion compound of a cyclic phenol sulfide and an organic halogen compound or a monocyclic aromatic compound can be regenerated by various processes. As the regeneration process, when the carrier is an ion exchange resin, for example, a process in which the carrier is treated with an aqueous alkaline solution, specifically, a process in which the inclusion compound is recovered and the carrier is regenerated by passing the aqueous alkaline solution through a column in the case of a column process, can be exemplified.

An organic halogen compound or a monocyclic aromatic compound can be separated and recovered efficiently using a separation recovering agent comprising the cyclic phenol sulfide of the present invention.

The present invention can be used in various applications, such as separation and recovery of an organic halogen compound or a monocyclic aromatic compound contained in tap water, underground water, soil water, sewage, waste water from factories, and the like.

In the medicinal use of the present invention, the compound represented by formula (4) may be used alone or as a mixture of two or more, and the compound represented by formula (4) may be used alone or together with other component, such as other antiviral agent (e.g., AZT and nelfinavir as anti-HIV agents) and the like.

The composition of the present invention comprises a compound represented by the above-described formula (4) or a pharmaceutically acceptable salt thereof and a pharmaceutically acceptable carrier or diluent.

In this case, the hydrocarbon group represented by X is preferably an alkyl group, Y is preferably —$SO_3M$, and M is a hydrogen atom, an alkyl group or a pharmaceutically acceptable base. The pharmaceutically acceptable base as used herein means a generally pharmaceutically acceptable base among the above-described substituents of M.

Also, the diluent is preferably a physiological saline.

The inclusion ratio of the compound represented by formula (4) and a physiological saline is optionally selected, but it may be within the range of generally from 1:100 to 100:1 as a weight ratio.

In the composition of the present invention, the compound represented by formula (4) may be used alone or as a mixture of two or more.

The administration amount of the pharmaceutical of the present invention is appropriately selected according to the usage, the degree of an injury, and the like. The cyclic phenol sulfide which is an effective ingredient in the present invention is usually administered to an adult orally or non-orally at a dose of from 10 mg to 1000 mg per kilogram of his/her weight per month once or a few times per day. Since the dosage depends on various factors as stated above, lower doses may be sufficient, or higher doses may be required.

The pharmaceutical of the present invention is generally used as a form of a medicament. The medicament can be selected from various forms according to the treatment object. Representative examples thereof include a tablet, a pill, powder, a liquid, a suspension, an emulsion, a granule, a capsule, a suppositorium, an injection (a liquid, a suspension, and the like), a drop, and the like.

The medicament is optionally prepared using a diluent or the like, other than the above physiological saline. When it is prepared as an injection, preferably, a liquid or a suspension is sterilized and has the same isotonicity with blood. When it is formulated into the liquid, emulsion and suspension, a diluent which is commonly used in this filed can be used. Examples thereof include water, water for injection, ethyl alcohol, propylene alcohol, ethoxylated isostearyl alcohol, polyoxylated isostearyl alcohol, and the like.

Additionally, examples of the carrier used in the pharmaceutical composition include glucose, fructose, sucrose, mannitol, lactose, starch, corn starch, cellulose, methyl cellulose, carboxymethyl cellulose, hydroxypropyl cellulose, alginic acid, talc, sodium citrate, calcium carbonate, calcium hydrogen phosphate, magnesium stearate, urea, a silicone resin, sorbitan fatty acid ester, glycerine fatty acid ester, and the like. They are appropriately selected according to the kind of the medicament.

The administration method of the pharmaceutical of the present invention to a patient is not particularly limited, and is carried out according to various preparation forms, the degree of disease, and the like. For example, in the case of a tablet, a pill, a liquid, a suspension, an emulsion, a granule, or a capsule, it is orally administered. Also, in the case of an injection, it is intravenously administered alone or as a mixture of a general fluid replacement, such as glucose, amino acids, or the like.

Next, the present invention will be illustrated in greater detail with reference to Production Examples and Examples, but it should be understood that the present invention is not construed as being limited thereto.

Production Example 1

Synthesis of 5,11,17,23-tetra-tert-butyl-25,26,27,28-tetrahydroxy-2,8,14,20-tetrathia[$19.3.1.1^{3,7}1^{9,13}1^{15,19}$]-octacosa-1(25),3,5,7(28),9,11,13(27),15,17,19(26),21,23-dodecaene (I)

To 45.2 g of 4-tert-butylphenol, 14.4 g elemental. sulfur and 3.0 g of sodium hydroxide were added, followed by heating up to 230° C. over 4 hours under stirring in an atmosphere of nitrogen, and then stirring for further 2 hours. During the reaction, water and a hydrogen sulfide generated by the reaction were eliminated. The water distilled during the reaction was about 0.8 g, and the hydrogen sulfide formed by the reaction was about 6 g. This reaction mixture was cooled to room temperature, dissolved in 500 ml of ether added, and hydrolyzed with a 1 N aqueous sulfuric acid solution. A separated ether layer was washed with water and dried with magnesium sulfate. The reaction mixture obtained after evaporation of ether was further partitioned by silica gel column chromatography (hexane/chloroform) to give a crude product. The crude product was recrystallized from chloroform/acetone to give 4.32 g of 5,11,17,23-tetra-tert-butyl-25,26,27,28-tetrahydroxy-2,8,14,20-tetrathia[$19.3.1.1^{3,7}1^{9,13}1^{15,19}$]-octacosa-1(25),3,5,7(28),9,11,13(27),15,17,19(26),21,23-dodecaene (I) as colorless transparent crystals.

This product is a cyclic alkylphenol sulfide of formula (2) in which $Y^1$=t-Bu (tert-butyl), Z=S, and n=4.

Physical properties of this product (I) are shown below.

Melting point: 320–322° C.

$^1$H-NMR: (δ, ppm, $CDCl_3$) 9.60 (s, 4H, OH), 7.64 (s, 8H, ArH), 1.22 (s, 36H, $C(CH_3)_3$)

$^{13}$C-NMR: (δ, ppm, $CDC_{13}$) 155.6, 144.7, 136.4, 120.5 (Ar), 34.2 ($\underline{C}(CH_3)$), 31.3(C($\underline{C}H_3)_3$)

IR: ($cm^{-1}$, KRS-5) 3324 (OH), 2962 (CH)

MS m/z: 720 ($M^+$)

Elemental analysis %: Calculated for $C_{40}H_{48}O_4S_4$: C, 66.62; H, 6.71; S, 17.79 Found: C, 66.50; H, 6.67; S, 17.84

Production Example 2

Synthesis of 5,11,17,23,29,35-hexa-tert-butyl-37,38, 39, 40,41,42-hexahydroxy-2,8,14,20,26,32-hexathia [$31.3.1.1^{3,7}1^{9,13}1^{15,19}1^{21,25}1^{27,31}$]dotetraconta-1(37), 3,5,7(42), 9,11,13(41),15,17,19(40),21,23,25(39),27, 29,31(38),33,35-octadecaene (II)

The reaction was carried out in the same manner as in Production Example 1, except that the reaction time was changed to 8 hours, and then the reaction mixture was partitioned by silica gel column chromatography (hexane/chloroform) to give a crude product. The crude product was recrystallized from chloroform/acetone to obtain 1.09 g of 5,11,17,23,29,35-hexa-tert-butyl-37,38,39,40,41,42-hexahydroxy-2,8,14,20,26,32-hexathia[$31.3.1.1^{3,7}1^{9,13}1^{15,19}1^{21,25}1^{27,31}$]dotetraconta- 1(37),3,5,7(42),9,11,13(41),15, 17,19(40),21,23,25(39),27,29,31(38),33,35-octadecaene (II) as white powder.

This product is a cyclic alkylphenol sulfide of formula (2) in which $Y^1$=t-Bu (tert-butyl), Z=S, and n=6.

Physical properties of this product (II) are shown below.

$^1$H-NMR: (δ, ppm, CDCl$_3$) 9.18 (s, 6H, OH), 7.59 (s, 12H, ArH), 1.23 (s, 54H, C(CH$_3$)$_3$)

$^{13}$C-NMR: (δ, ppm, CDCl$_3$) 155.3, 144.4, 135.4, 120.4 (Ar), 34.2 ($\underline{C}$(CH$_3$)$_3$), 31.3 (C($\underline{C}$H$_3$)$_3$) MS m/z: 1080 (M$^+$)

Elemental analysis %: Calculated for $C_{60}H_{72}O_6S_6$: C, 66.62; H, 6.71; S, 17.79 Found: C, 66.20; H, 6.57; S, 17.12.

EXAMPLE 1

Synthesis of a sodium salt of 25,26,27,28-tetrahydroxy-2,8,14,20-tetrathia[$19.3.1.1^{3,7}1^{9,13}1^{15,19}$]octacosa-1(25),3,5,7(28),9,11,13(27),15,17,19 (26),21,23-dodecaene-5,11,17,23-tetrasulfonic acid (III)

In 30 ml of concentrated sulfuric acid, 200 mg of 5,11, 17,23-tetra-tert-butyl-25,26,27,28-tetrahydroxy-2,8,14,20-tetrathia[$19.3.1.1^{3,7}1^{9,13}1^{15,19}$]octacosa-1(25),3,5,7 (28),9, 11,13(27),15,17,19(26),21,23-dodecaene (I) of formula (2) wherein $Y^1$=t-Bu and n=4, obtained in Production Example 1 was suspended, followed by heating up to 80° C. for 4 hours for reaction. After the reaction solution was allowed to stand for cooling, it was diluted up to 100 ml with purified water, unreacted material (I) was removed by filtration, and sodium chloride was added thereto, followed by salting out to give white powder (197 mg, 78%). By further carrying out the salting out several times, 141 mg of white product (III) was obtained. The yield was 56%.

This product (III) is a cyclic phenol compound of formula (1) in which X=H, Z=S, M=Na, and n=4.

Its physical properties are shown below.

Melting point: 370–390° C. (decomposed point)

$^1$H-NMR: (δ, ppm, 25 mg/0.6 ml D$_2$O) 8.87 (s, 8H, ArH)

$^{13}$C-NMR: (δ, ppm, 25 mg/0.6 ml D$_2$O) 164.27, 139.43, 138.93, 124.85 (Ar)

FAB-MS(m/z):903 (M)$^-$

Elemental analysis %: Calculated for $C_{24}H_{12}Na_4O_{16}S_8$: C, 31.86; H, 1.34; Na, 10.16; S, 28.35 Found: C, 31.5; H, 1.6; Na, 10.1; S,28.7.

EXAMPLE 2

In 50 ml of concentrated sulfuric acid, 5.02 g of 5,11,17, 23-tetra-tert-butyl-25,26,27,28-tetrahydroxy-2,8,14,20-tetrathia[$19.3.1.1^{3,7}1^{9,13}1^{15,19}$]octacosa-1(25),3,5,7(28),9, 11,13(27),15,17,19(26),21,23-dodecaene (I) of formula (2) wherein $Y^1$=t-Bu and n=4 obtained in Production Example 1 was suspended, followed by heating up to 80° C. for 22 hours for reaction. After the reaction solution was allowed to stand for cooling, the reaction solution was diluted up to 500 ml with purified water, unreacted material (I) was removed by filtration and sodium chloride was added thereto, followed by salting out to give white powder (5.35 g, 85%). By further carrying out the salting out several times, 5.02 g of white product (III) was obtained. The yield was 80%.

This product (III) is a cyclic phenol compound of formula (1) in which X=H, Z=S, M=Na, and n=4.

EXAMPLE 3

Synthesis of sodium 37,38,39,40,41,42-hexahydroxy-2,8,14,20,26,32-hexathia[$31.3.1.1^{3,7}1^{9,13}1^{15,19}1^{21,25}1^{27,31}$]-dotetraconta-1(37),3,5,7(42),9, 11,13(41),15,17,19(40),21,23,25(39),27,29,31(38), 33,35-octadecaene-5,11,17,23,29,35-hexasulfonate (IV)

In 20 ml of concentrated sulfuric acid, 1.0 g of 5,11,17, 23,29,35-hexa-tert-butyl-37,38,39,40,41,42-hexa-hydroxy-2,8,14,20,26,32-hexathia[$31.3.1.1^{3,7}1^{9,13}1^{15,19}1^{21,25}1^{27,31}$]dotetraconta-1(37),3,5,7(42),9,11,13(41),15,17,19(40),21, 23,25(39),27,29,31(38),33,35-octadecaene (II) of formula (2) wherein $Y^1$=t-Bu and n=6 obtained in Production Example 2 was suspended, followed by heating up to 95° C. for 16 hours for reaction. After the reaction solution was allowed to stand for cooling, the thus formed precipitate was collected by filtration, and the precipitate was dissolved in 30 ml of purified water. Unreacted material (I) which did not dissolved in purified water was removed by filtration, and sodium chloride was added thereto, followed by salting out to give white powder (920 mg, 73%). This powder was recrystallized from purified water-ethanol to give 840 mg of white product (IV) The yield was 67%.

This product (IV) is a cyclic phenol compound of formula (1) in which X=H, Z=S, M=Na, and n=6.

Its physical properties are shown below.

$^1$H-NMR: (δ, ppm, 20 mg/0.6 ml D$_2$O) 7.63 (s, 12H, ArH)

$^{13}$C-NMR: (δ, ppm, 20 mg/0.6 ml D$_2$O) 159.24, 138.38, 133.02, 124,34 (Ar)

FAB-MS (m/z): 1357 (M$^{+2}$)$^-$

Elemental analysis %: Calculated for $C_{36}H_{18}Na_6O_{24}S_{12}$: C, 31.86; H, 1.34; Na, 10.16; S, 28.35 Found: C, 31.6; H, 1.5; Na, 10.1; S,28.0

EXAMPLE 4

Using the cyclic phenol sulfide (III) of formula (1) in which X=H, Z=S, M=Na and n=4 (X=H, Y=SO$_3$Na, Z=S and n=4 in formula (4)) obtained in Example 1, organic-halogen compounds was separated by sedimentation.

Firstly, the cyclic phenol sulfide (III) was dissolved in heavy water to prepare its heavy water solution having a concentration of 25 mM, and the heavy water solution was saturated with each of chloroform, methylene chloride, 1,2-dichloroethane, and 1,1,2,2-tetrachloroethane. The solution was stirred at room temperature for 5 hours, followed by salting out with sodium chloride, and the thus formed precipitate was collected by filtration.

Next, when each of the thus obtained precipitates was dissolved in heavy water and $^1$H-NMR measurement was carried out, it was confirmed that each precipitate contained the cyclic phenol sulfide (III) and each of the organic halogen compounds.

Molar ratios (calculated from the proton ratio of $^1$H-NMR) of the cyclic phenol sulfide (III) and each of the organic halogen compounds obtained by sedimentation are shown in Table 1.

TABLE 1

| Organic halogen compound | Molar ratio in precipitate (cyclic phenol sulfide (III): organic halogen compound) |
|---|---|
| Chloroform | 1:1.0 |
| Methylene chloride | 1:1.9 |
| 1,2-Dichloroethane | 1:1.1 |
| 1,1,2,2-Tetrachloroethane | 1:0.9 |

EXAMPLE 5

By changing a concentration of the cyclic phenol sulfide (III) in a solution, changes in the amount of recovered organic halogen compounds were calculated.

The cyclic phenol sulfide (III) was dissolved in heavy water to various concentrations. Each of the heavy water solutions was saturated with each of the organic halogen compounds in the same manner as described in Example 4, followed by stirring at room temperature for 5 hours.

The heavy water phase was separated from the organic halogen compound phase, and $^1$H-NMR measurement of the heavy water phase was carried out to calculate changes in the concentration of the organic halogen compounds contained in each heavy water. As a comparison, the same procedure was repeated using heavy water containing no cyclic phenol sulfide (III), and the amount of the organic halogen compounds dissolved in heavy water was corrected.

The results are shown in FIG. 1$a$ to FIG. 1$d$. The abscissa is a concentration of the added cyclic phenol sulfide (III), and the ordinate is a concentration of organic halogen compound in heavy water after stirring.

When the concentration of the cyclic phenol sulfide (III) in heavy water was increased, the amount of the organic halogen compounds present in the heavy water by forming an inclusion compound with the cyclic phenol sulfide (III) was also increased. Also, the molar ratio of the cyclic phenol sulfide (III) and the organic halogen compounds, which can be deduced from the slopes of FIG. 1$a$ to FIG. 1$d$, coincided with the values calculated in Example 1. That is, the ratio was 1:1 in the case of chloroform, 1,2-dichloroethane and 1,1,2,2-tetrachloroethane, and 1:2 in methylene chloride.

EXAMPLE 6

An aqueous solution was prepared by dissolving the cyclic phenol sulfide (III) obtained in Example 1 (X=H, Z=S, M=Na, and n=4 in formula (1) (X=H, Y=SO$_3$Na, Z=S, and n=4 in formula (4))) and chloroform in purified water to give a final concentration of each compound of 5 mM. In the same manner, an aqueous solution was prepared by dissolving the cyclic phenol sulfide (III) and dichloromethane in purified water to give a final concentration of each compound of 5 mM. Separately, an aqueous solution solely containing 5 mM of chloroform was prepared, and an aqueous solution solely containing 5 mM of dichloromethane was also prepared.

Next, four glass columns were prepared by packing each column with 20 ml of a weakly basic anion exchange resin, and 25 ml of each of the above-described four aqueous solutions was passed through each column at a flow rate of 2.0 ml/min. Concentrations of chloroform and dichloromethane in the aqueous solutions at the column outlet were calculated by GC-MS measurement to compare the decreasing ratio of the concentration of the organic halogen compounds.

As a result, the concentration of chloroform in the aqueous solution containing the cyclic phenol sulfide (III) and chloroform decreased to about $6 \times 10^{-5}$ in comparison with the case of the aqueous solution of chloroform only, and the concentration of dichloromethane in the aqueous solution containing the cyclic phenol sulfide (III) and dichloromethane decreased to about $2 \times 10^{-5}$ in comparison with the case of the aqueous solution of dichloromethane only.

EXAMPLE 7

In the same manner as described in Example 6, a glass column was packed with 20 ml of a weakly basic anion exchange resin, and 25 ml of an aqueous solution prepared by dissolving the cyclic phenol sulfide (III) produced by the production example (X=H, Z=S, M=Na, and n=4 in formula (1) (X=H, Y=SO$_3$Na, Z=S and n=4 in formula (4))) in purified water to give a final concentration of 5 mM was passed through the column at a flow rate of 2.0 ml/min.

Next, each of chloroform and dichloromethane was added as an organic halogen compound separately to purified water to prepare aqueous solutions containing 5 mM of them, respectively, and 25 ml of each aqueous solution was passed through the above-described column at a flow rate of 2.0 ml/min.

Each of concentrations of chloroform and dichloromethane in the aqueous solutions at the column outlet was calculated by GC-MS measurement and compared with concentrations of the organic halogen compounds when they were passed through columns not treated with the cyclic phenol sulfide (III) to calculate their decreasing ratio.

As a result, chloroform was decreased to a concentration of about $8 \times 10^{-5}$ and dichloromethane was decreased to a concentration of about $3 \times 10^{-5}$ when they were passed through columns treated with the cyclic phenol sulfide (III).

EXAMPLE 8

A cytotoxic test was carried out using the cyclic phenol sulfide (III) obtained in Example 1 (X=H, Z=S, M=Na, and n=4 in formula (1) (X=H, Y=SO$_3$Na, Z=S, and n=4 in formula (4))).

Cytotoxic Test

Figure 2:
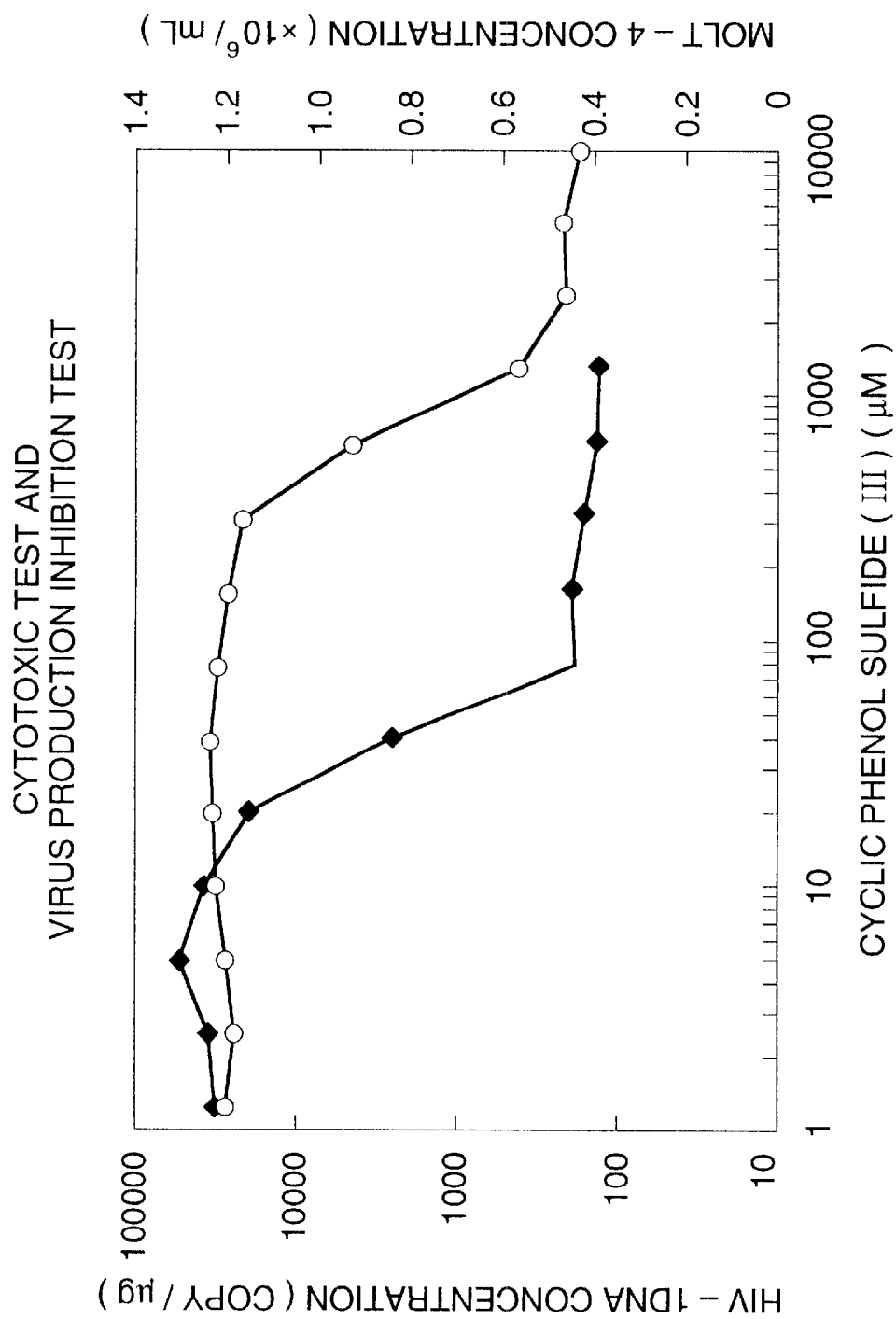
FIG. 2 is a graph showing a relationship between a concentration of a cyclic phenol sulfide (III) and a concentration of HIV-1 DNA after 3 days of infection. The symbol ♦ indicates an HIV-1 DNA concentration, and o indicates an MOLT-4 concentration.

In order to evaluate cytotoxicity of the cyclic phenol sulfide (III) in a human cell line, MOLT-4 (T cell leukemia cell, Riken Gene Bank accession number RCB 0206), was used in the test. The cyclic phenol sulfide (III) was dissolved in a medium (RPMI-1640 containing 10% FCS (fetal calf serum), kanamycin (5,000 U/ml) and streptomycin (5 mg/ml)) to a concentration of 2.5 mM, and the solution was made into 2-fold serial dilutions to prepare cyclic phenol sulfide (III)-containing medium samples having 11 steps of concentration. Each of the cyclic phenol sulfide (III)-containing medium samples was dispensed into wells of a 6-well plate in 2.5 ml, a MOLT-4 culture broth of $2 \times 10^5$ cells/ml was dispensed into the resulting wells in 2.5 ml, the cells were cultured at 37° C. for 3 days in a moist incubator containing 5% CO$_2$, and then theced density was measured using Celltac MEK-5254 (manufactured by NIHON KOHDEN). A relation of the MOLT-4 cell density 3 days after culturing to the concentration of cyclic phenol sulfide (I) is shown in FIG. 2. Based on this drawing, the CC$_{50}$ value was calculated to be 700 μM.

EXAMPLE 9

A virus production inhibition test was carried out using the cyclic phenol sulfide (III) obtained in Example 1 (X=H, Z=S, M=Na and n=4 in formula (1) (X=H, Y=SO$_3$Na, Z=S and n=4 in formula (4))).

Virus Production Inhibition Test

The cyclic phenol sulfide (III) was dissolved in the medium used in Example 8 to a concentration of 2.5 mM, and the solution was made into 2-fold serial dilutions to prepare cyclic phenol sulfide (III)-containing medium samples having 11 steps of concentration. Each of the cyclic phenol sulfide (III)-containing medium samples was dispensed into wells of a 6-well plate in 2.5 ml, a culture broth containing $1.64 \times 10^5$ cells/ml of MOLT-4 or $1.82 \times 10^4$ cells/ml of HIV-1-infected MOLT-4 was dispensed into the resulting wells in 2.5 ml, the cells were cultured at 37° C. for 3 days in a moist incubator containing 5% CO$_2$, the resulting cell density was measured using Celltac MEK-5254 (manufactured by NIHON KOHDEN), and then a portion of the medium containing $10^6$ cells was taken out to purify DNA. The number of HIV-1 DNA contained in 500 ng of the cell DNA was determined by competitive nested PCR.

The primers used were JA12, JA9 and JA10 and JA11 described by J. Albert et al. in *J. Clin. Microbiol.*, 28: 1560 (1990) and by S. Kato et al. in *J. Viro. Process* (1998, in press), and the competitor used was a preparation containing fragments of the nucleotide numbers 6201 to 7118 and 7242 to 8805 of an HIV-1 DNA clone, NL4-3, described by S. Kato et al. in *J. Virol. Process* (1998, in press). Firstly, 500 ng of each cell DNA sample was mixed with 1 μM of the primers JA9 and JA12, 0.2 mM dNTP, 50 mM KCl, 10 mM Tris-HCl (pH 8.3), 4 mM MgCl$_2$, 5,000 copies of the competitor and 2 units of Taq DNA polymerase manufactured by Roche), and the total volume was adjusted to 100 μl with Milli-Q water.

This solution was subjected to the first PCR (30 cycles, 1 cycle being 94° C. for 15 seconds, 64° C. for 30 seconds and 72° C. for 60 seconds), and then a 1/50 volume of the product was mixed with 1 μM of the primers JA10 and JA11B and subjected to the second PCR (25 cycles, 1 cycle being 94° C. for 15 seconds, 64° C. for 30 seconds and 72° C. for 60 seconds). In this case, a standard authentic sample was prepared using 5,000 copies of wild type HIV-1 DNA instead of 500 ng of each of the cell DNA samples. The thus obtained PCR product was subjected to 2% agarose gel electrophoresis, and then the gel was stained with ethidium bromide to carry out UV photographing. The thus obtained image was analyzed using BioImage Analysis Soft (manufactured by Nihon BioImage Ltd.) to obtain intensity ratio of the wild type HIV-1 band and the competitor band, and concentration of HIV-1 DNA in the sample was calculated based on the result.

A relation of the concentration of HIV-1 DNA after 3 days of infection to the concentration of cyclic phenol sulfide (III) is shown in FIG. 2. Based on this drawing, the IC$_{50}$ value was calculated to be 40 μM.

Based on the results of Example 8 and Example 9, the cyclic phenol sulfide (III) has a therapeutic ratio (=CC$_{50}$/IC$_{50}$) of 18. Also, its concentration range for inhibiting HIV production almost completely but not showing cell injury was from 70 μM to 300 μM.

EXAMPLE 10

When a composition was produced by mixing the cyclic phenol sulfide (III) with a physiological saline at a weight ratio of 1:9, and the test similar to Example 8 was repeated using the composition, the similar result of Example 8 was obtained.

Industrial Applicability

The cyclic phenol sulfide of the present invention can be used as a metal scavenger, an ion sensor, a separation membrane material, a substrate-specific sensor, a phase-transfer catalyst, an artificial enzyme, a light energy conversion material, or an intermediate of a functional molecule capable of recognizing an ion or a molecule, particularly, it can separate an organic halogen compound or a monocyclic aromatic compound efficiently. Also, according to the present invention, a cyclic phenol sulfide sulfonic acid compound and a salt thereof can be produced efficiently and easily by reacting a cyclic alkylphenol sulfide with sulfuric acid.

The pharmaceutical of the present invention has antiviral activities, particularly an activity against retrovirus, such as HIV or the like, shows low cytotoxicity, and can be produced by a simple and easy process. Additionally, the composition of the present invention can be used as a pharmaceutical.

What is claimed is:

1. A sulfonic acid compound of a cyclic phenol sulfide represented by formula (1):

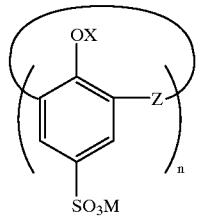

(1)

(wherein X represents a hydrogen atom, a hydrocarbon group, or an acyl group;

M represents a hydrogen atom, an alkyl group, a metal, an ammonium, a (lower-alkyl)ammonium, a (lower-alkanol)ammonium, a nitrogen-containing heterocyclic group, or an amino acid residue;

Z represents Sm, SO, or SO$_2$;

m is an integer of from 1 to 7; and n is an integer of from 4 to 12, with the proviso that the plural X's, M's and Z's are each the same or different, and at least one of the plural M's is neither a hydrogen atom nor an alkyl group).

2. A process for producing sulfonic acid of a cyclic phenol sulfide or a salt thereof, comprising reacting a cyclic alkylphenol sulfide represented by formula (2):

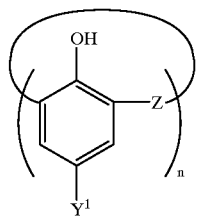

(2)

(wherein Y$^1$ represents an alkyl group, Z represents Sm, SO, or SO$_2$; m is an integer of from 1 to 7; and n is an integer of from 4 to 12) with sulfuric acid to produce sulfonic acid of a cyclic phenol sulfide represented by formula (3):

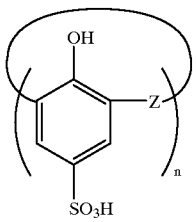

(3)

(wherein Z and n have the same meanings as defined above) or a salt thereof.

3. A composition for separating and recovering an organic halogen compound or a monocyclic aromatic compound, comprising a compound represented by formula (4):

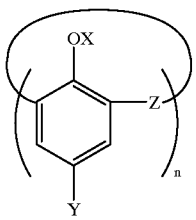

(4)

(wherein X represents a hydrogen atom, a hydrocarbon group, or an acyl group;

Y represents a hydrogen atom, a hydrocarbon group, a halogenated hydrocarbon group, —$COR^1$, —$OR^2$, —$COOR^3$, —CN, —$CONH_2$, —$NO_2$, —$NR^4R^5$, a halogen atom, —$SO_4R^6$, —$SO_3R^7$, or —$SO_3M$;

$R^1$ to $R^7$ are each a hydrogen atom or a hydrocarbon group; and

M represents a hydrogen atom, an alkyl group, a metal, an ammonium, a (lower-alkyl)ammonium, a (lower-alkanol)ammonium, a nitrogen-containing heterocyclic group, or an amino acid residue;

with the proviso that the plural M's are the same or different, and at least one of the plural M's is neither a hydrogen atom nor an alkyl group;

Z represents Sm, SO, or $SO_2$;

m is an integer of from 1 to 7;

n is an integer of from 4 to 12, with the proviso that the plural X's, Y's and Z's are each the same or different), or a salt thereof, and a carrier.

4. A process for separating and recovering an organic halogen compound or a monocyclic aromatic compound, comprising bringing a compound represented by formula (4) or a salt thereof into contact with an organic halogen compound or a monocyclic aromatic compound to separate and recover the organic halogen compound or the monocyclic aromatic compound.

5. The process according to claim 4, wherein the contact is carried out by mixing the compound represented by formula (4) or a salt thereof with the organic halogen compound or the monocyclic aromatic compound.

6. The process according to claim 4, wherein the contact is contact of the organic halogen compound or the monocyclic aromatic compound with a carrier, wherein the compound represented by formula (4) or a salt thereof has mixed with or deposited on the carrier.

7. The process according to claim 4, wherein the contact is contact of a solution containing an organic halogen compound or a monocyclic aromatic compound in which the compound represented by formula (4) or a salt thereof has been dissolved, with a carrier.

8. A composition, comprising the compound represented by formula (4) of claim 3 or a pharmaceutically acceptable salt, and a pharmaceutically acceptable carrier or diluent.

9. The composition according to claim 8, wherein the diluent is a physiological saline.

10. A method for preventing or treating a disease derived from virus production, comprising administering an effective amount of the compound represented by formula (4) of claim 3 or a pharmaceutically acceptable salt thereof to a human or an animal.

11. A method for selectively inhibiting virus production, comprising administering an effective amount of a compound represented by formula (4) or a pharmaceutically acceptable salt thereof to cells.

12. The method of claim 10 or 11, wherein the virus is HIV.

* * * * *